United States Patent
Chu et al.

(10) Patent No.: US 6,293,909 B1
(45) Date of Patent: Sep. 25, 2001

(54) DEVICE AND METHOD OF USING A SURGICAL ASSEMBLY WITH MESH SHEATH

(75) Inventors: Michael S. H. Chu, Brookline; Yem Chin, Burlington, both of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/285,447

(22) Filed: Apr. 2, 1999

Related U.S. Application Data

(63) Continuation of application No. 09/130,784, filed on Aug. 7, 1998, now Pat. No. 5,916,145.

(51) Int. Cl.[7] ............... A61B 1/005; A61B 1/00
(52) U.S. Cl. ............................... 600/121; 600/124
(58) Field of Search ................. 600/121, 122, 600/123, 124, 149, 139, 140, 143

(56) References Cited

U.S. PATENT DOCUMENTS

| | | | |
|---|---|---|---|
| 4,301,790 | 11/1981 | Bol et al. ........................... | 600/125 |
| 4,646,722 | 3/1987 | Silverstein et al. . | |
| 4,721,097 | 1/1988 | D'Amelio . | |
| 4,741,326 | 5/1988 | Sidall et al. . | |
| 4,878,485 | 11/1989 | Adair ................................. | 600/123 |
| 4,899,787 | 2/1990 | Ouchi et al. ...................... | 138/131 |
| 4,914,521 | 4/1990 | Adair ................................. | 600/122 |
| 4,991,564 | 2/1991 | Takahashi et al. . | |
| 4,991,565 | 2/1991 | Takahashi et al. . | |
| 5,050,585 | 9/1991 | Takahashi . | |
| 5,105,800 | 4/1992 | Takahashi et al. . | |
| 5,159,919 | 11/1992 | Chikama ........................... | 600/124 |
| 5,201,908 | 4/1993 | Jones ................................. | 600/123 |
| 5,237,984 | 8/1993 | Williams, III et al. . | |
| 5,257,617 | 11/1993 | Takahashi . | |
| 5,259,366 | 11/1993 | Reydel et al. . | |
| 5,329,935 | 7/1994 | Takahashi . | |
| 5,356,416 | 10/1994 | Chu et al. ......................... | 606/140 |
| 5,364,353 | 11/1994 | Corfitsen et al. ................. | 600/140 |
| 5,386,817 | 2/1995 | Jones . | |
| 5,406,939 | 4/1995 | Bala . | |
| 5,413,092 | 5/1995 | Williams, III et al. . | |
| 5,429,118 | 7/1995 | Cole et al. ........................ | 600/121 |
| 5,431,676 | 7/1995 | Dubrul et al. .................... | 606/185 |
| 5,483,951 | 1/1996 | Frassica et al. .................. | 600/104 |
| 5,496,259 | 3/1996 | Perkins ............................. | 600/124 |
| 5,569,161 | 10/1996 | Ebling et al. .................... | 600/121 |
| 5,704,899 | 1/1998 | Milo ................................. | 600/123 |
| 5,746,694 | 5/1998 | Wilk et al. ....................... | 600/123 |
| 5,916,145 | * 6/1999 | Chu et al. ........................ | 600/121 |

FOREIGN PATENT DOCUMENTS

WO 92/12680   6/1992   (WO) .

* cited by examiner

Primary Examiner—Paul J. Hirsch
(74) Attorney, Agent, or Firm—Finnegan, Henderson, Farabow, Garrett & Dunner, L.L.P.

(57) ABSTRACT

An endoscopic assembly, utilizing a braided mesh material as an expandable sheath, is disclosed. The mesh sheath is adapted to receive an endoscope for viewing the interior of a body cavity or lumen and one or more channels for performing medical procedures within the patient. The mesh sheath expands laterally as it is compressed longitudinally, which allows it to come into contact with the interior of the body cavity. By doing so, it can anchor the assembly, take samples from the body cavity, or dilate a stricture in the body cavity. Additional dilation procedures can be performed by removing the endoscope and inserting other instruments without removing the entire assembly from the patient. The body cavity can be hermetically sealed to reduce the risk of contamination of the endoscope and channels.

36 Claims, 16 Drawing Sheets

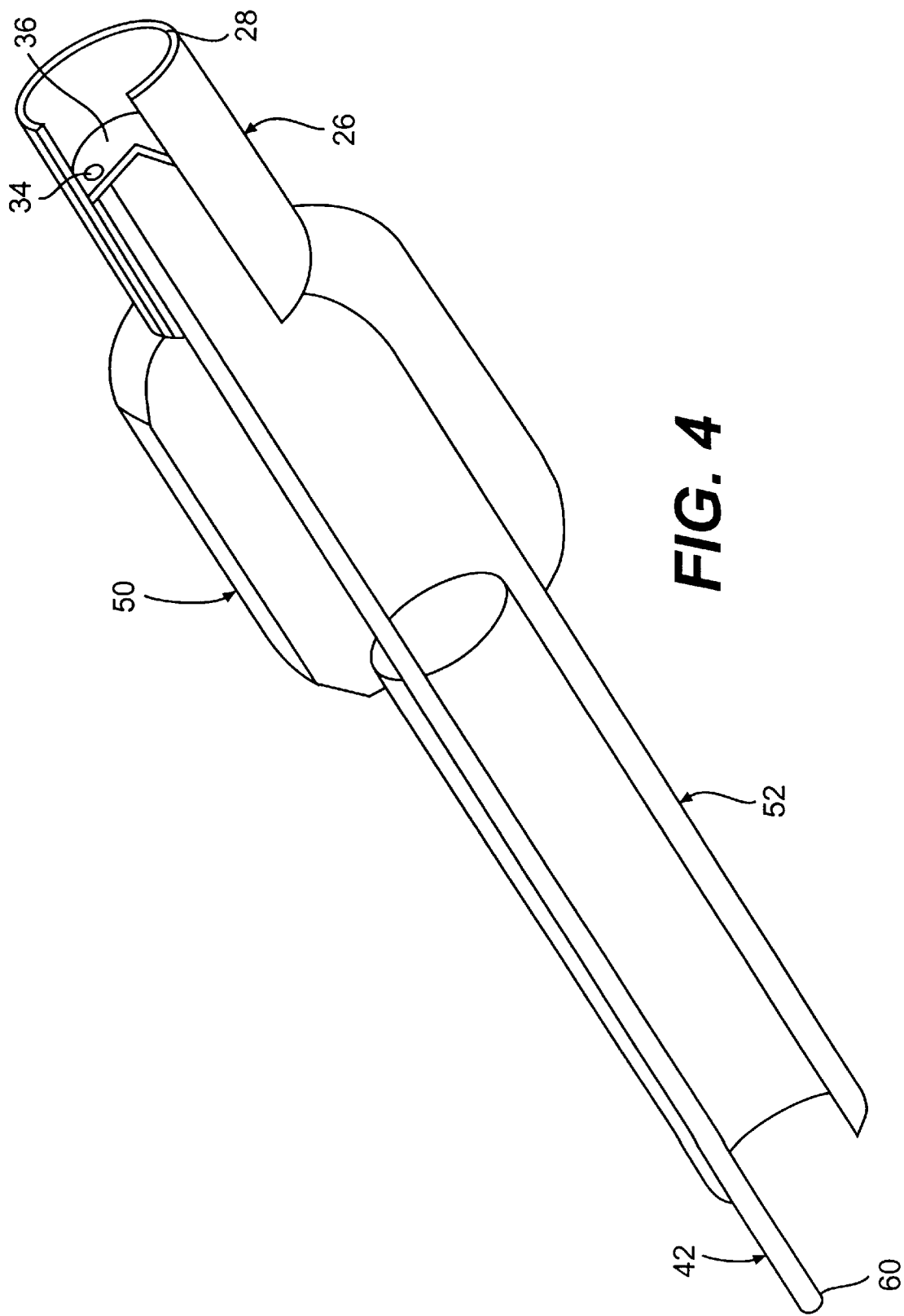

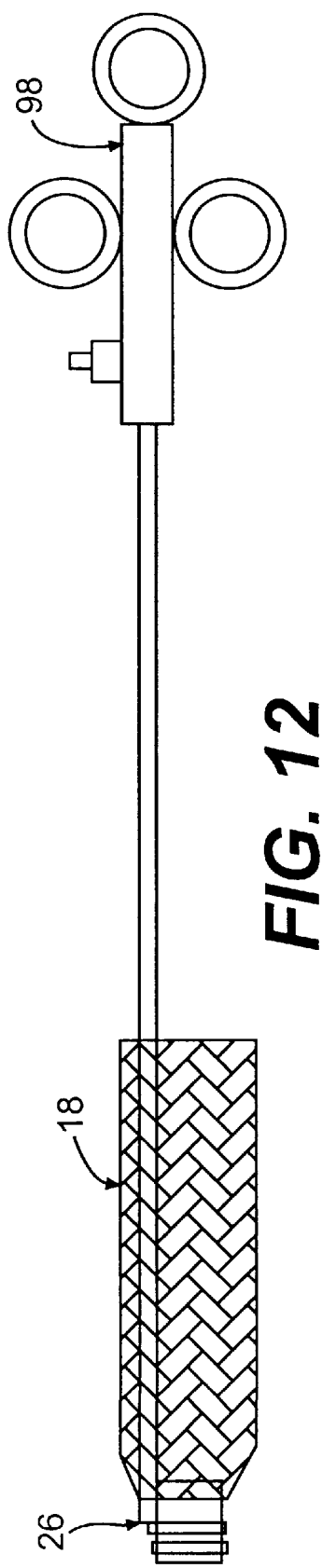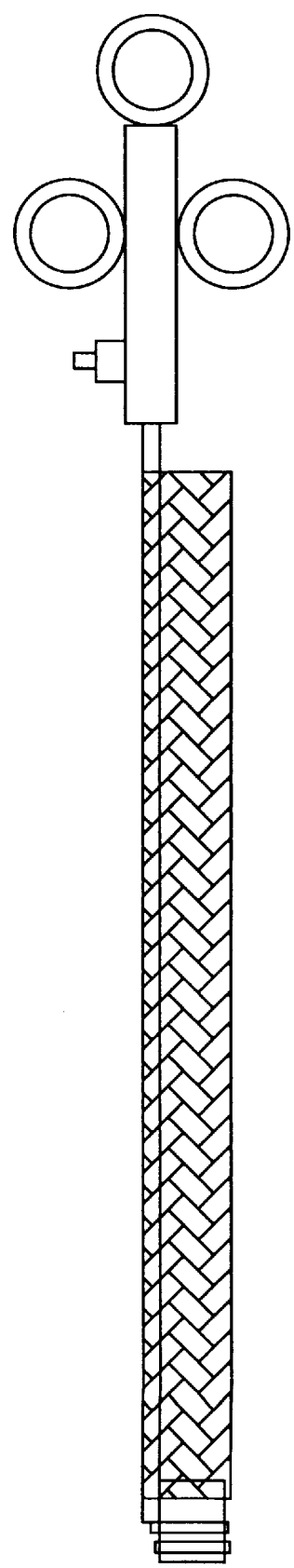

DEVICE AND METHOD OF USING A SURGICAL ASSEMBLY WITH MESH SHEATH

This is a continuation of application Ser. No. 09/130,784, filed Aug. 7, 1998, now U.S. Pat. No. 5,916,145 all of which is incorporated herein by reference.

BACKGROUND OF THE INVENTION

A. Field of the Invention

The present invention relates to surgical assemblies, and more particularly, to assemblies for enclosing surgical scopes in flexible sheaths.

B. Description of the Prior Art

A variety of surgical scopes are used in medical procedures within a patient's body. For example, endoscopes are used for viewing the interior of a body cavity or a hollow organ. They are often categorized by the part of the body they are used to examine, such as the esophagus, stomach, colon, and blood vessels. Endoscopes have been combined with complementary devices into endoscopic assemblies to perform various functions within a patient's body more efficiently. A sheath is often used to enclose the endoscope with these other devices into a unitary endoscopic assembly.

In addition to a sheath, the endoscopic assembly may include multiple channels or passages, sometimes referred to as working channels, that allow several functions to be performed at the distal end of the assembly. The endoscope and working channels are often disposed within the sheath, with the working channels arranged around the perimeter of the endoscope. The endoscope itself does not necessarily have working channels, but may contain a visual imaging device, illumination devices, and control wires that bend the distal end of the endoscope and any working channels attached to it. Various functions can be performed with endoscopic assemblies having channels, including providing air, water and suction, or the taking of biopsies when the appropriate instruments are introduced through the channels of the endoscopic assembly. Accessories such as those used when taking a specimen typically have an elongated flexible shaft and jaws or other cutting instruments operatively connected to the shaft's distal end.

Sheaths may serve several additional purposes in a surgical assembly, including enclosing endoscopic assemblies. For example, the endoscope, as well as any working channels, need to remain together, in a single unit, when in the patient to allow for easy movement through the interior of a patient. Sheaths can be used to hold the assembly together within the body, with the endoscope and any working channels disposed within the sheath. In addition, sheaths are used to protect the assembly from contamination that can occur during an endoscopic procedure wherein the assembly contacts body tissues and fluids within the patient. Proper cleaning and sterilization of the assembly is very laborious and costly, which reduces the cost effectiveness of performing the endoscopic procedures. In response to the contamination problem, disposable endoscopic sheaths have been developed. The disposable sheaths fit over the endoscope and completely isolate it from the contaminating environment. The distal ends of the working channels are left open to allow for the passage of air, water, suction or endoscopic accessories through the channels to the patient.

Existing assemblies with sheaths, some containing multiple channels, can allow more than one task to be performed at the same time. For example, the sheath can reduce contamination while the channels are used to perform a biopsy. However, additional tasks cannot be completed without first removing the endoscope from the patient and then inserting another instrument or instruments to perform the additional task. For example, to dilate a passageway, an endoscope may be used to view the area to be dilated, but then the endoscope would have to be removed and another instrument such as a balloon catheter would need to be inserted to carry out the dilation procedure. Such processes increase the likelihood of contamination, the time required to complete a procedure and the cost due to the need to purchase separate instruments for each procedure. Accordingly, there is a need for an endoscopic assembly that can carry out multiple tasks without requiring the removal of instruments from the body.

SUMMARY OF THE INVENTION

The present invention is directed to a surgical assembly that provides improved capability to perform other functions while the assembly remains in the patient. The present invention accomplishes this result by increasing the capabilities and functionality of a sheath used to enclose an endoscope and/or other surgical devices being placed internally in a patient.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention, in one embodiment, comprises a sheath for enclosing a surgical scope, the sheath comprising an elongated flexible tube adapted to coaxially surround a surgical scope; one or more elongated passages aligned axially within the tube; the elongated tube being adapted for axial extension or contraction to either lengthen or shorten the length of the tube while respectively diminishing or enlarging the radial dimensions thereof.

In another embodiment, the present invention provides a surgical assembly comprising an elongated flexible outer tube; a scope coaxially disposed within the elongated tube; one or more elongated passages aligned axially within the outer tube; the elongated outer tube being adapted for axial extension to lengthen or retraction to shorten the length of the tube while respectively diminishing or enlarging the radial dimensions thereof. The assembly may also include channels running alongside the endoscope that are open on each end to allow for medical instruments to be used at the distal end of the assembly within the patient. A distal housing may also be disposed at a distal end of the assembly, the housing having a suction chamber and an endoscope entry chamber. The mesh sheath may be hermetically sealed to reduce contamination of the assembly and channels.

The present invention also provides a method of using a surgical assembly having an elongated flexible outer tube, the outer tube being adapted for axial extension to lengthen or retraction to shorten the length of the tube while respectively diminishing or enlarging the radial dimensions thereof, comprising the steps of placing an endoscope having a distal end within an elongated flexible tube; inserting the tube, with the endoscope disposed within it, into a body cavity of a patient for viewing the interior of the body cavity; and using the endoscope to view through a window in a distal housing disposed at the distal end of the assembly.

Another method of using the assembly includes using the channels within the assembly to perform procedures within the body cavity of the patient. Additional methods expand the diameter of the mesh sheath by dilating the sheath with cylindrical rods in place of the endoscope, with a dilation balloon, or by compressing the sheath longitudinally to cause the sheath to expand laterally.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 4 is a perspective view of the present invention with a distal portion of the sheath expanded.

FIG. 12 is a side view of the mesh sheath in its compressed state with its diameter expanded.

FIG. 13 is a side view of the mesh sheath in its relaxed state.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

A preferred embodiment of the invention utilizes a mesh material. The mesh material used in accordance with the invention expands in diameter laterally as it is compressed longitudinally and contracts in diameter as it is kept in tension longitudinally or allowed to return to its relaxed state. Mesh materials useful in the invention, for example, are manufactured by Bentley Harris and distributed by Schaal™. The mesh is typically made of polyester in a cylindrical braided configuration. The mesh is formed by overlapping strands of flexible or semi-rigid material, crosswoven over and under each other in generally clockwise and counterclockwise directions. The mesh is such that a counterclockwise strand is able to slidably and intersectingly move with respect to a generally clockwise strand. The maximum diameter of the expanded mesh is dependent upon the extended length and the pitch of the mesh tube.

The biocompatibility of the mesh material makes it suitable for use in diagnostic and therapeutic applications. The mesh can be shaped and set to a configuration as described above. Alternatively, in the case of a plastic mesh, the mesh can be set in a desired configuration by dipping it into hot water at a temperature of 100 degrees C. for a period of 10 minutes. The capabilities of the material render it particularly well suited for the objects of the present invention. It is to be understood, however, that other flexible mesh materials having the requisite characteristics are also suitable in the invention. Depending on the application, the mesh could be made of stainless steel, nylon, polyurethane, urethanes or any other biocompatible material. For tamponade, the mesh should be a relatively soft material. For tissue gathering, the mesh should be stiffer.

Figure 1:
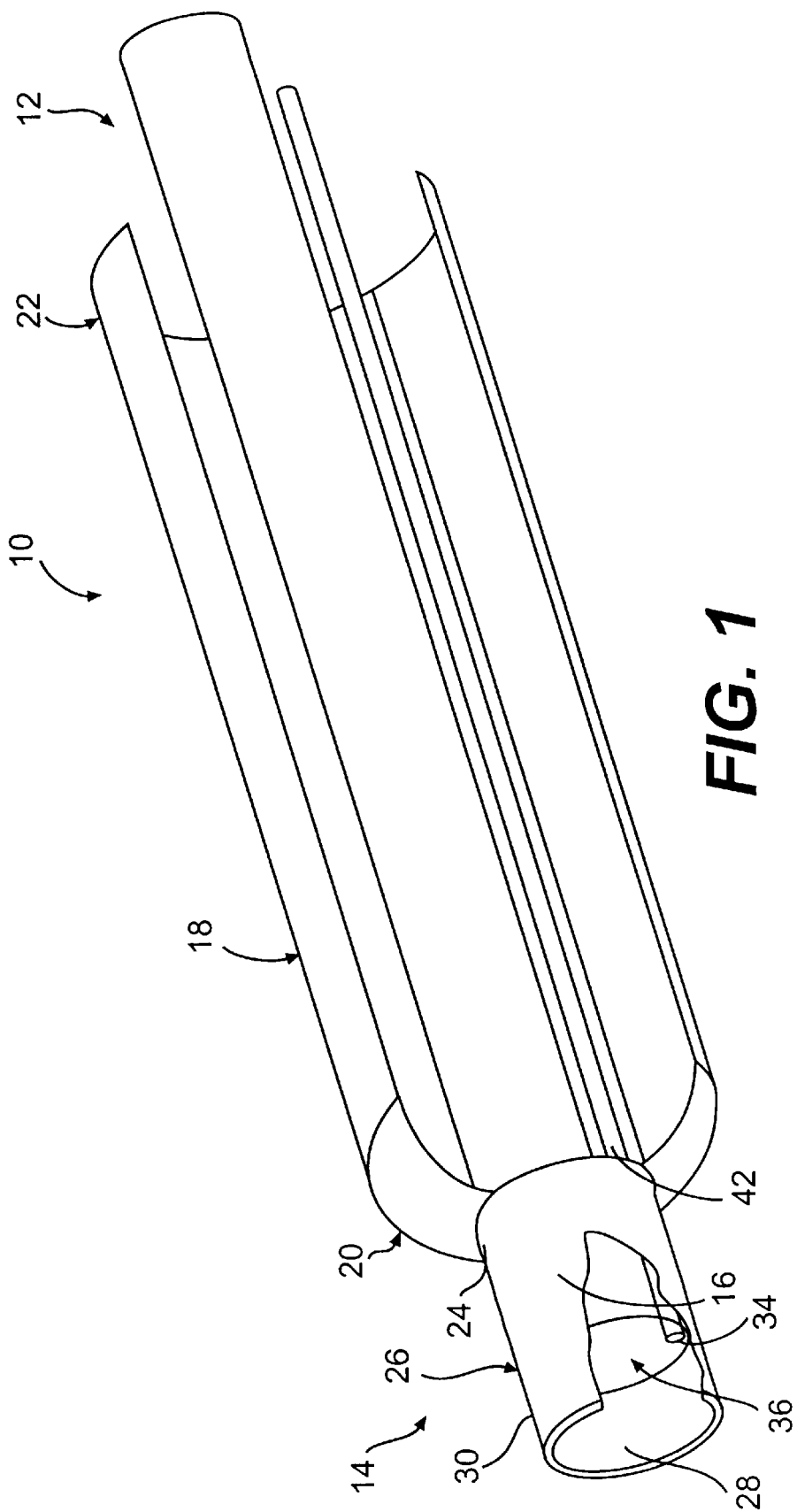
FIG. 1 is a perspective view of the present invention with the sheath partially cut away.
Figure 1A:
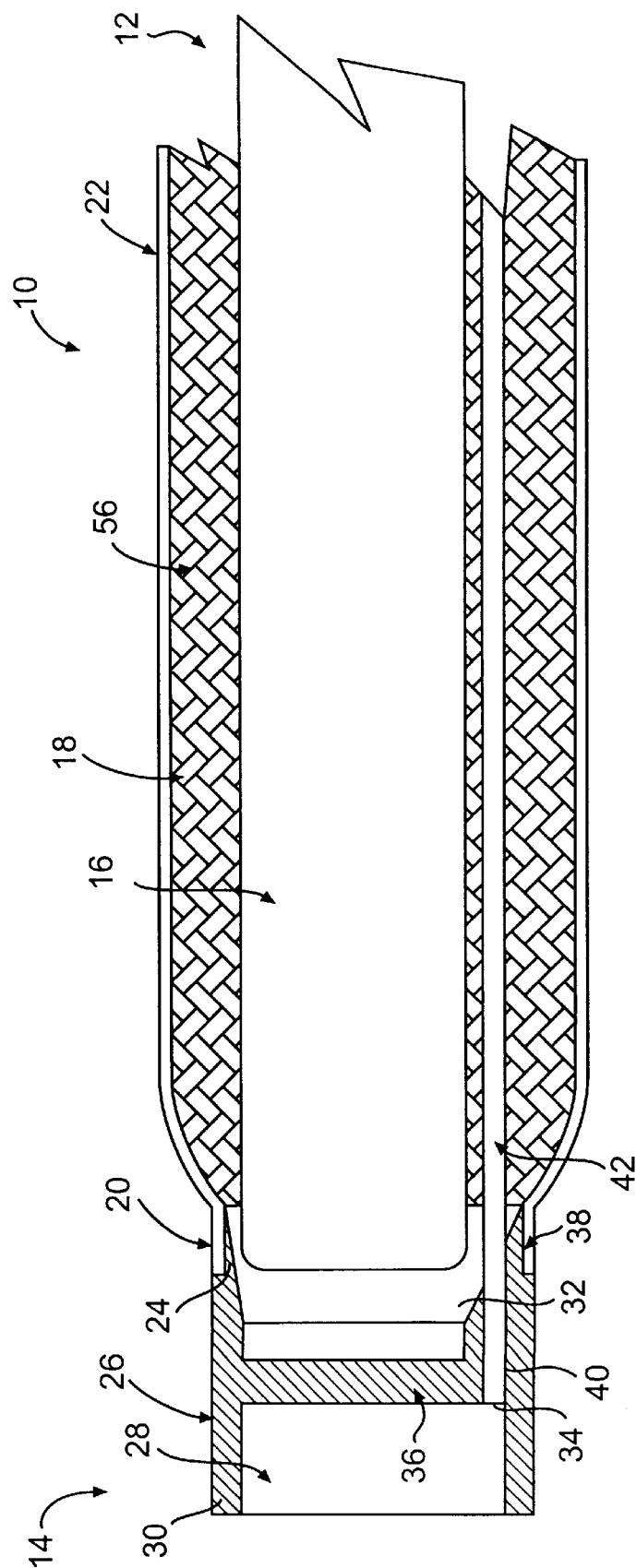
FIG. 1A is a cross section of a side view of the present invention.
Figure 1B:
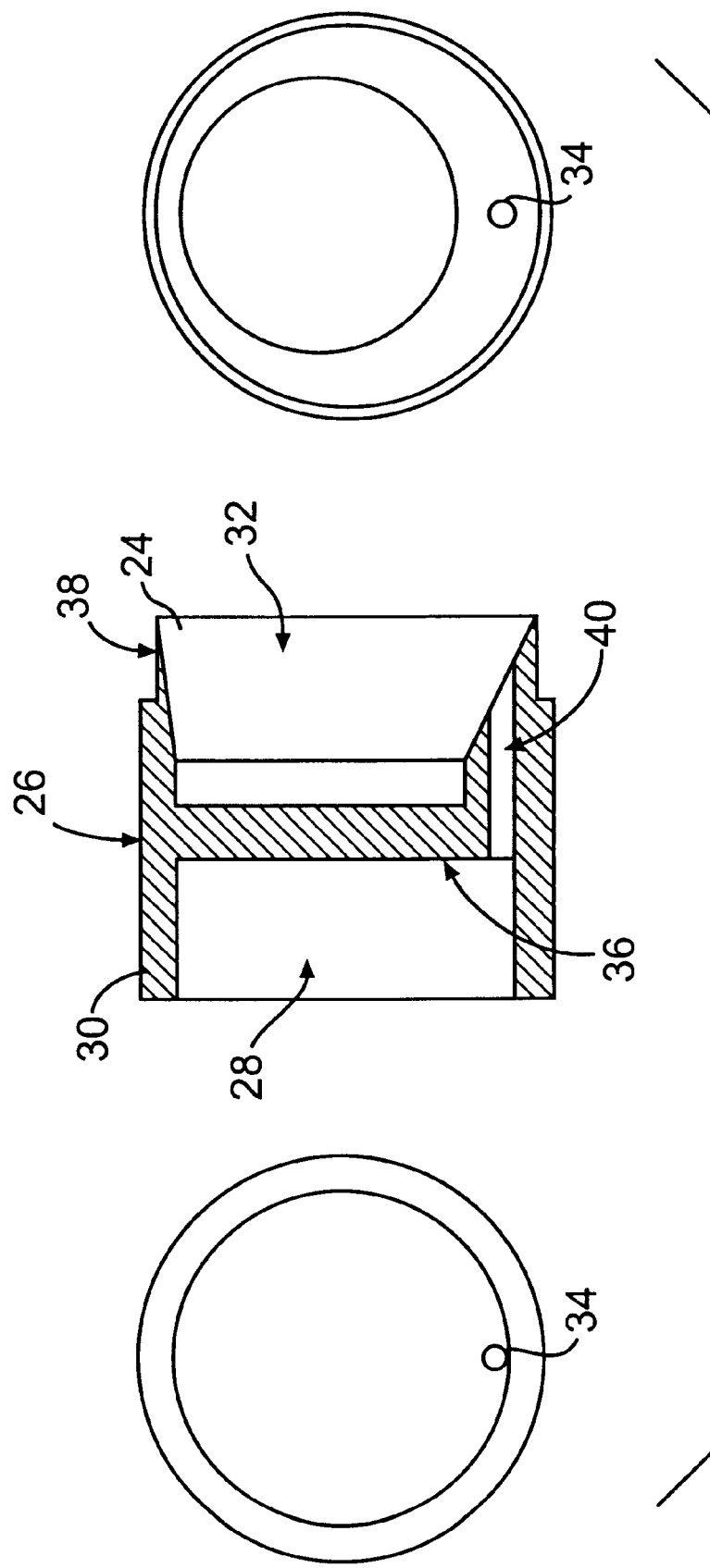
FIG. 1B is a detail of the distal end of the present invention.

Referring first to FIGS. 1, 1A and 1B, which illustrate one embodiment of the present invention, the surgical assembly, in this case an endoscopic assembly 10, is shown with a proximal end 12 and distal end 14. An endoscope 16 is shown within an elongated flexible tube in the configuration of a mesh sheath 18. The mesh sheath 18 has a distal end 20 attached to a proximal end 24 of a distal housing 26. The mesh sheath 18 in FIGS. 1 and 1A is in a compressed state, with its diameter larger than the diameter of the endoscope 16.

The distal housing 26 includes a suction chamber 28 on its distal end 30 and a tapered endoscope entry chamber 32 on its proximal end 24. Between the endoscope entry chamber 32 and the suction chamber 28 is a clear window 36 through which a person using the endoscope 16 can view a desired area of the patient. A mesh sheath mating surface 38 is provided on the proximal end 24 of the distal housing 26, the mating surface 38 having a slightly smaller diameter than the rest of the distal housing 26. One or more lumens 40 may be provided in the distal housing 26 to accommodate one or more working channels 42, the lumen 40 passing through the distal housing 26 between the tapered endoscope entry chamber 32 and the suction chamber 28. The channel 42 runs the length of the assembly 10 alongside the endoscope 16. The channel 42 terminates at the distal end 14 of the assembly at the channel port 34. The channel 42 and lumen 40 could accommodate medical instruments, supply air and water, or provide suction.

In most cases the mesh sheath 18 is introduced into the body in a collapsed form over a endoscope 16, and is converted into its expanded configuration inside the body by the use of a channel and/or pull wire (both indicated by 42).

The channel and/or pull wire 42 is held at the proximal end 12 of the assembly 10, while the sheath 18 is pushed toward the distal end 14 to form the expanded configuration. A channel (tube) has a lumen through it, whereas a pull wire does not. A pull wire is used when there is no need for a lumen, thus reducing the profile of the assembly 10, or to add strength to the channel tubing. The pull wire 42 is attached to the distal housing and runs the length of the device similar to channel 42. The channel and/or pull wire 42 are needed to expand or convert the sheath 18 into its expanded configurations, especially when the distal end 14 of the assembly 10 is in the body. The sheath 18 is expanded by holding the channel and/or pull wire 42 at its proximal end 60 (FIG. 3) and pushing the sheath 18 toward its distal end 20 to expand its diameter and converting it to its expanded configuration. To collapse the expanded diameter, the sheath 18 is pulled toward proximal end 60.

Figure 2:
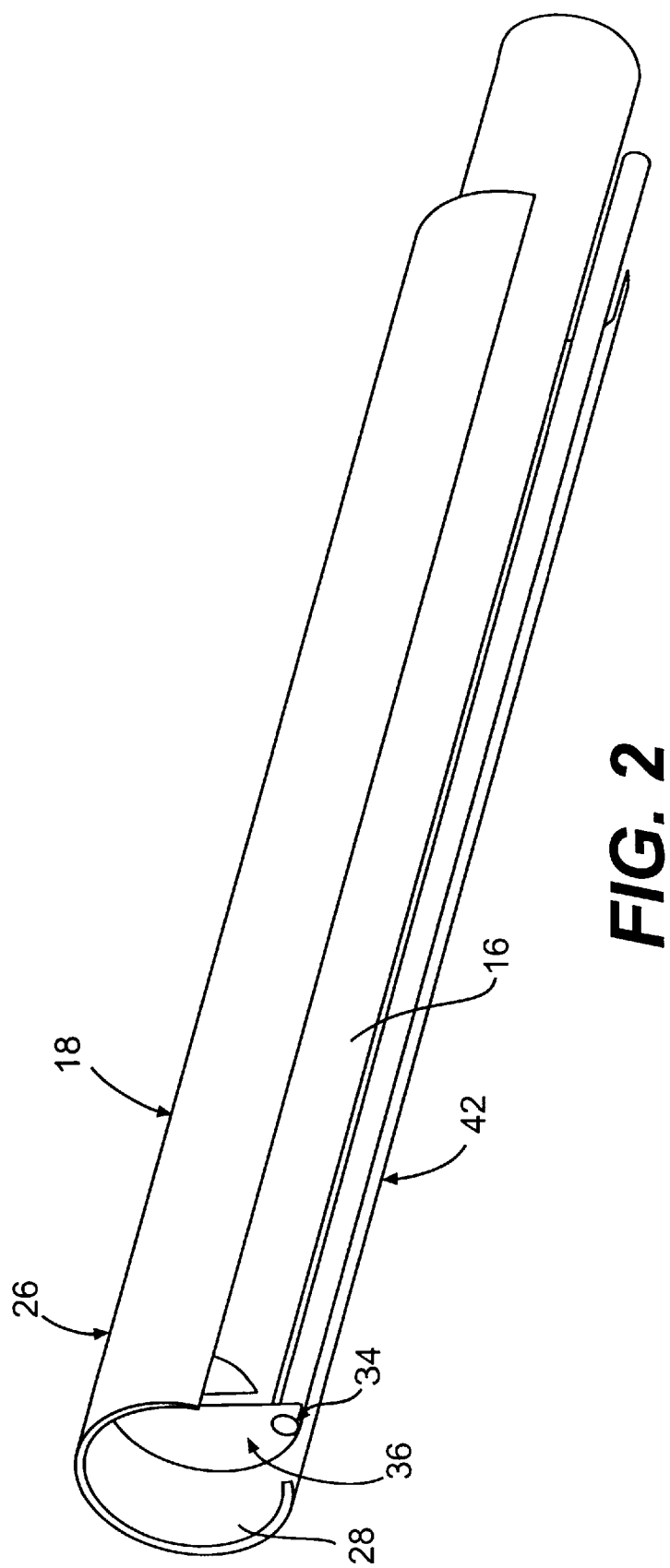
FIG. 2 is a perspective view of the present invention with the sheath partially cut away.
Figure 2A:
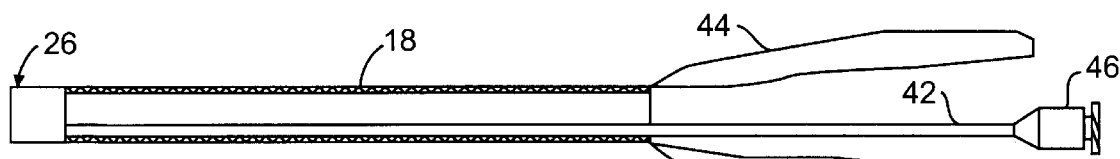
FIG. 2A is a side view of the present invention with the sheath in a first position.
Figure 2B:
FIG. 2B is a side view of the present invention with the sheath in a second position.

FIGS. 2, 2A and 2B show the assembly 10 with the mesh sheath 18 in its relaxed state, with its diameter just greater than the diameter of the endoscope 16 (not shown) and any channels 42 (not shown) within it. The mesh sheath 18 may be pulled in tension from its proximal end by pulling on the mesh itself or using a means attached to the proximal end to do so. In one preferred embodiment, elastic bands 44 are attached to a proximal end 22 of the mesh sheath 18 to enable one to pull the mesh sheath into tension. When the mesh sheath 18 is in tension, or when the diameter of the endoscope 16 and channels 42 within it are greater than the diameter of the sheath 18 in its relaxed state, the sheath 18 exerts a radial compression force on the endoscope 16 and any channels 42 within it. The amount of force applied by the sheath 18 and the diameter at which it begins applying the force can be varied by selecting sheaths 18 of various types, sizes, and rigidities. The rate at which the sheath 18 expands as compressed can also be controlled and monitored while the assembly 10 is in the patient.

Figure 2C:
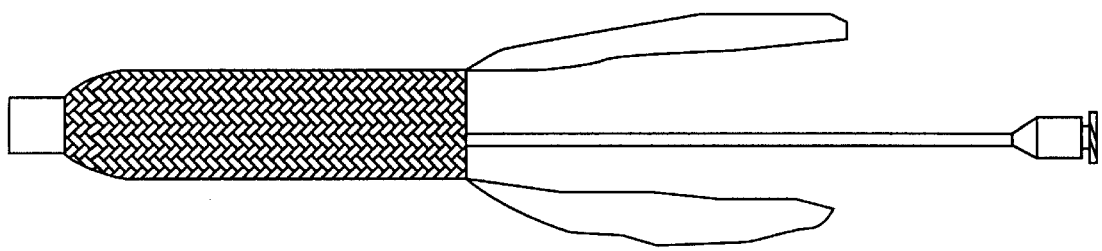
FIG. 2C is a side view of the present invention with the sheath in a third position.

FIGS. 2A, 2B and 2C also show a connector 45 attached to the channel 42. The connector 46 can then be attached to other devices that nay supply air, water, suction or instruments. In FIG. 2C, the mesh sheath 18 is shown in a compressed (diameter expanded), as opposed to the relaxed state shown in FIGS. 2A and 2B.

Figure 3:
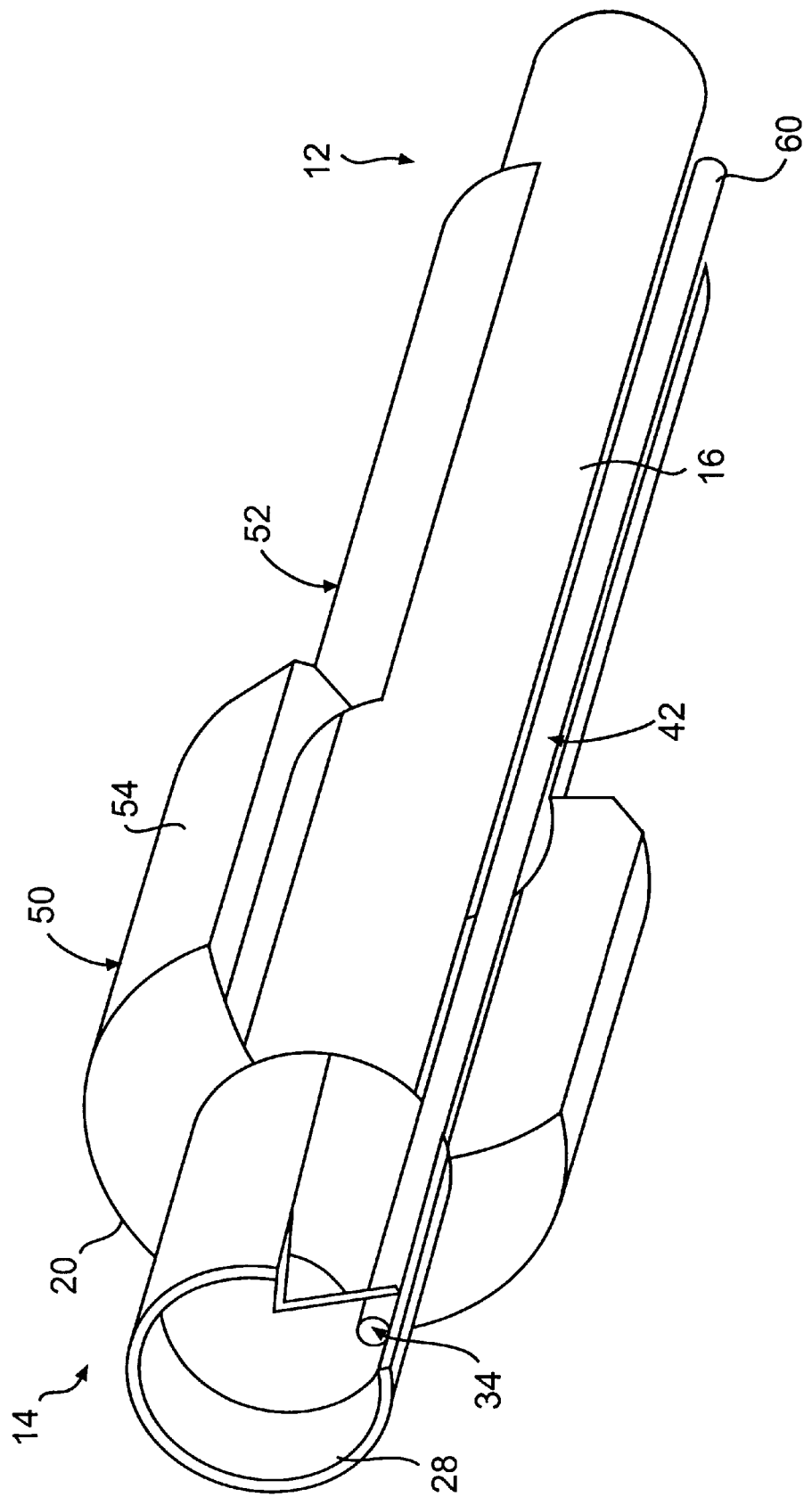
FIG. 3 is a perspective view of the present invention with a distal portion of the sheath expanded.
Figure 3A:
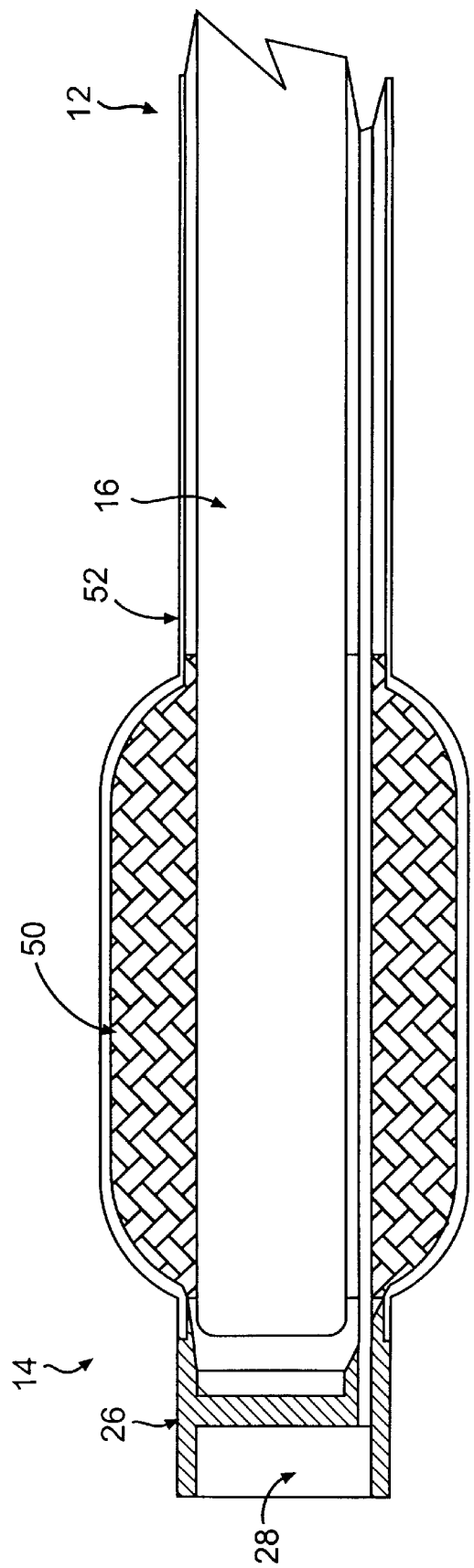
FIG. 3A is a cross section of a side of the present invention with a distal portion of the sheath expanded.

FIGS. 3, 3A, 4 (without endoscope) and 5 (with additional channels) show another embodiment of the present invention. In this embodiment, only the distal end 20 of the sheath 18 is able to expand. The sheath 18 comprises two portions, a distal portion 50 and a proximal portion 52. The distal portion 50 is coated by an elastic rubber or plastic material 54, so that it is gas- and liquid-impervious, yet still allows the mesh strands 56 (FIG. 1A) to move within the mesh sheath 18 when compressed or when relaxed. Alternatively, the distal portion 50 of the sheath 18 can be without a coating to allow gas and liquids to pass while the distal portion 50 of the sheath 18 is expanded. The proximal portion 52 of the sheath 18 is not able to expand or contract as it is compressed. Instead, the proximal portion 52 of the sheath 18 transmits the compressive force to the distal portion 50 of the sheath 18, causing it to expand. A flexible tube may be used for this purpose and attached to the distal portion 50 of the sheath 18. Alternatively, the proximal portion 52 of the sheath 18 may be a continuation of the distal portion 50 of the mesh sheath 18, but coated with a plastic material that prevents the proximal portion 52 of the sheath 18 from expanding laterally. If a coated mesh is to be used for the proximal portion 52 of the sheath 18, it should be sized large enough so that the endoscope 16 and channel 42 can pass easily through the sheath 18.

Figure 5:
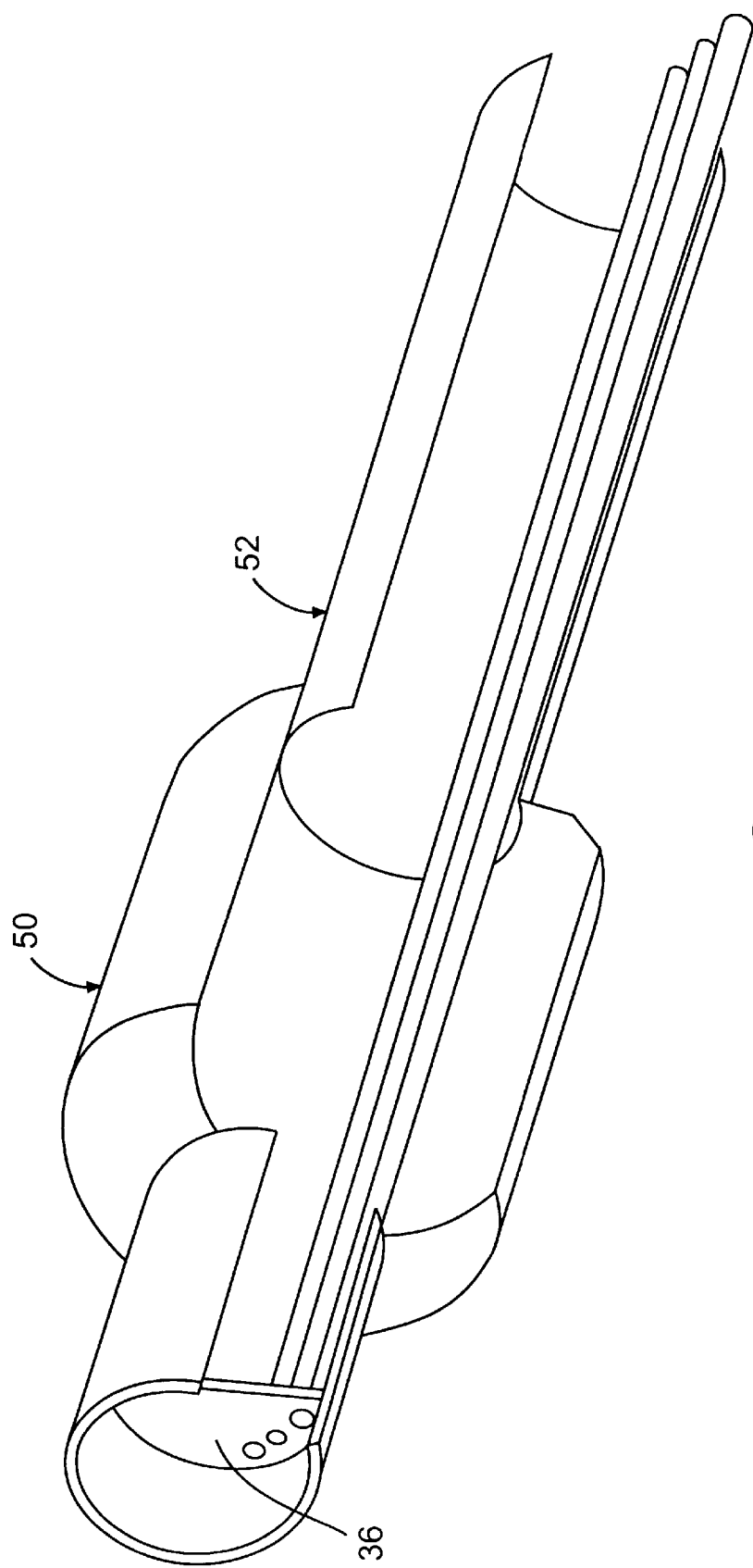
FIG. 5 is a perspective view of the present invention with a distal portion of the sheath expanded and working channels that can be used for stabilizing the tamponade.

FIGS. 3–5 illustrate an alternative embodiment which can be used in accordance with a method whereby the distal portion 50 of the sheath 18 is expanded while the proximal portion 52 of the sheath 18 maintains the same diameter. For example, in one method, the channel 42 is held at its proximal end 60 external to the human body, while the proximal portion 52 of the sheath 18 is pushed toward the distal portion 50 of the sheath 18. The proximal portion 52 of the sheath 18 transfers the force to compress and shorten the distal portion 50 of the sheath 18 in length and expanding its outer and inner diameters laterally. This function can serve several purposes. For example, the expanded distal portion 50 of the sheath 18 can be used to anchor or stabilize the endoscope 16 in the gastrointestinal tract, to occlude the distal end 14 of the endoscopic assembly 10 from the proximal end 12 of the endoscopic assembly 10 or to tamponade a bleeding lesion. FIG. 5 shows the expanded sheath 18 configuration that can be used for used for stabilizing the tamponade. The surface of the expanded distal portion 50 of the sheath 18 would cover and apply pressure against the tract wall to tamponade any bleeder. This configuration could also anchor the assembly 10 within the tract. The expanded diameter of the sheath 18 against the tract wall would prevent the assembly 10 from migrating in the tract.

Figure 6:
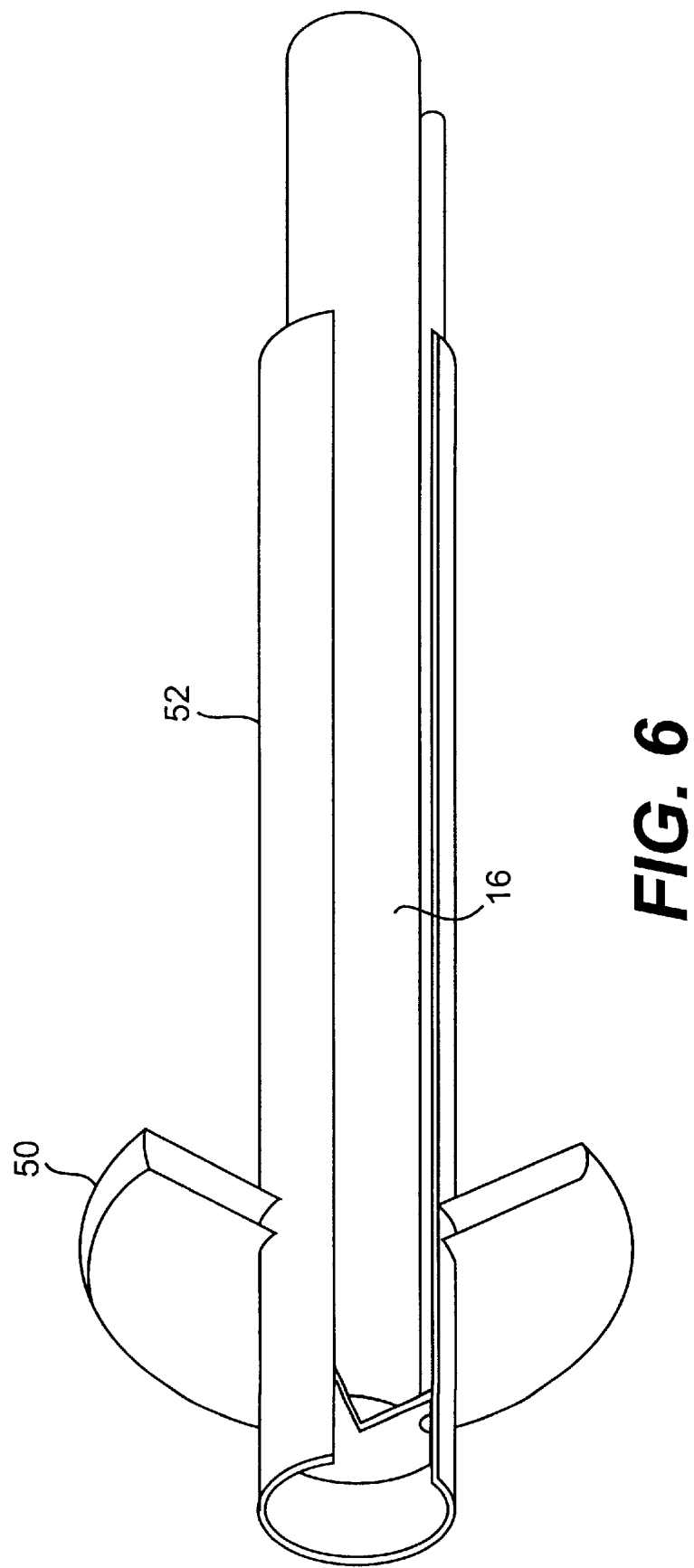
FIG. 6 is a perspective view of the present invention with a distal portion of the sheath expanded that can be used for stabilizing, retrieval, or tamponade.
Figure 7:
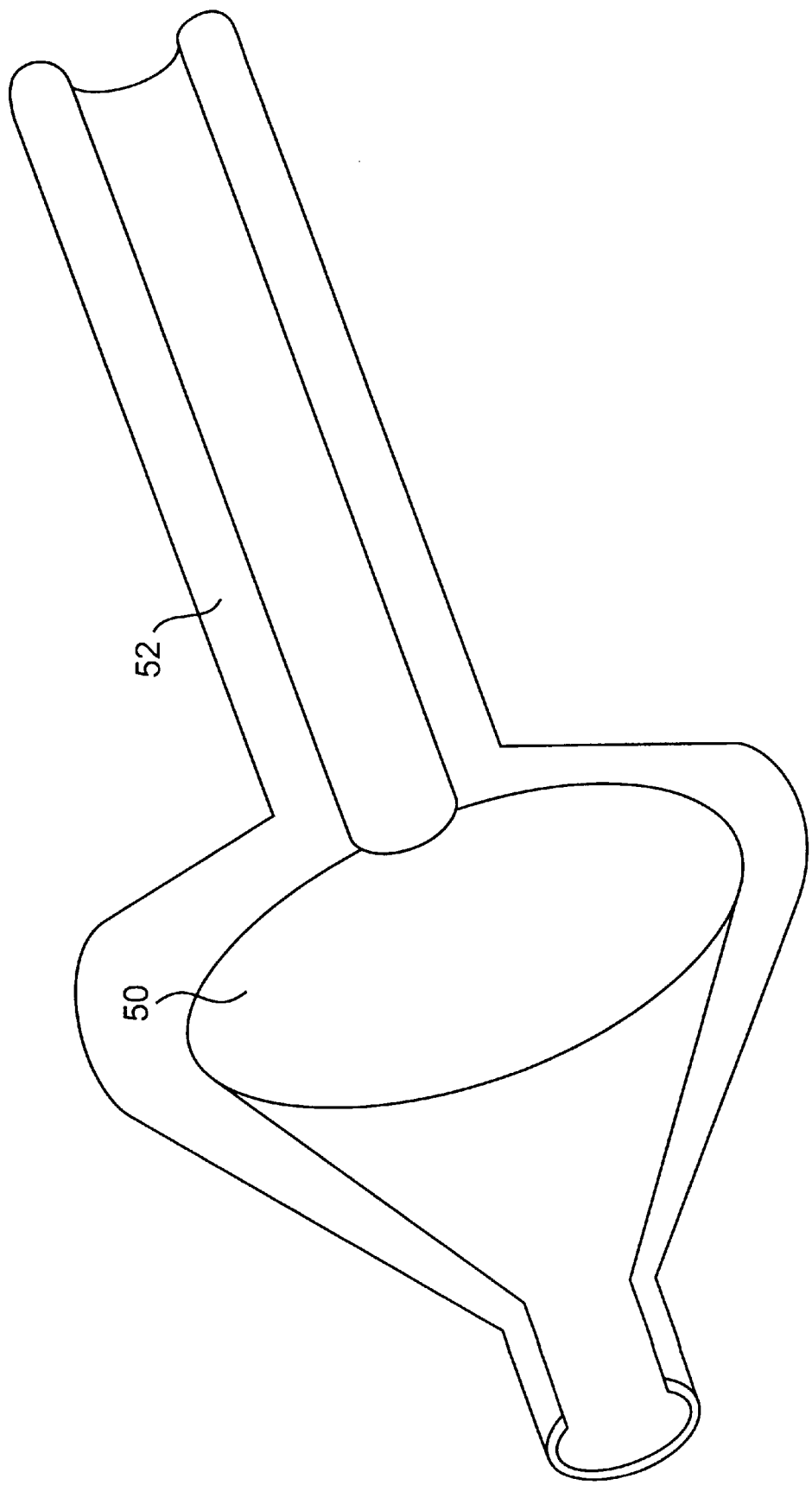
FIG. 7 is a perspective view of the present invention with a distal portion of the sheath expanded that can be used for stabilizing, retrieval, or tamponade.
Figure 8:
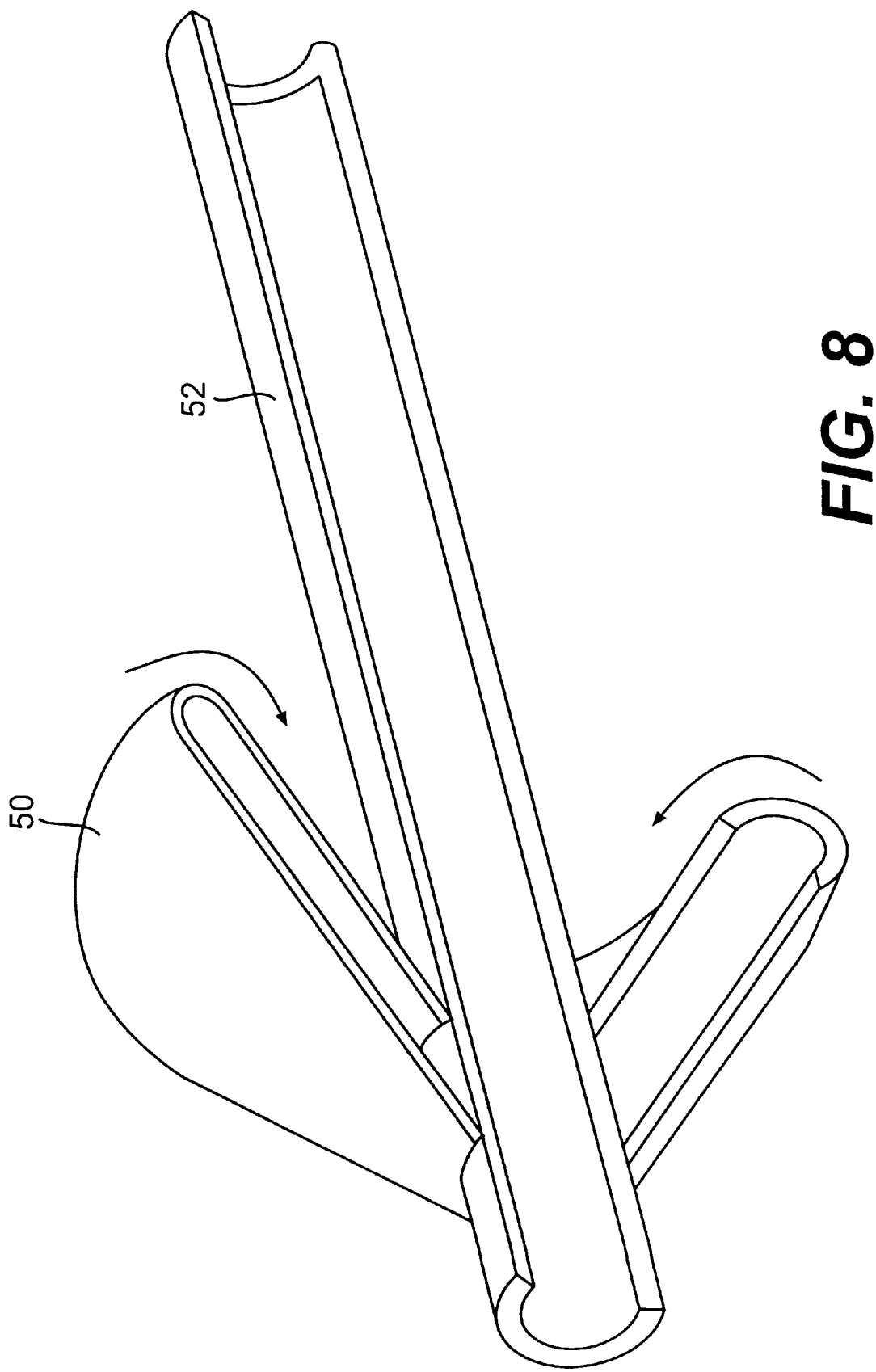
FIG. 8 is a perspective view of the present invention with a distal portion of the sheath expanded that can be used for stabilizing, retrieval, or tamponade.

FIGS. 6, 7 and 8 show the assembly 10 in different configurations that could be used for retrieval. FIG. 6 shows the expanded sheath 18 open distal to a battery in the gastrointestinal tract. The battery is retrieved by pulling the entire expanded assembly 10 proximal and out of the body. In this configuration the expanded sheath 18 is also preventing the passage of fluid from one side of the expanded sheath 18 to the other. The configuration of the invention shown in FIG. 7 could be used similar to that of FIG. 6 for retrieval or can be used as a dilator to be pushed distally to open strictures in a tract. In this configuration, the assembly 10 is expanded proximal to the stricture, which avoids dilating the entire proximal tract. The taper towards the distal end 20 of the mesh sheath 18 is pushed into the stricture to be dilated. The configuration of the invention shown in FIG. 8 is in its expanded state, scraping the walls of the gastrointestinal tract, collecting cell or tissue samples as the assembly 10 is pulled proximal. The samples are shown to fall into the center catch area of the expanded sheath 18 for retrieval.

In each embodiment of the present invention, the endoscope 16 is removable and can be exchanged for an instrument such as a balloon catheter (not shown) to dilate a stricture underneath the distal end 20 of the sheath 18. When a balloon catheter is used, the mesh sheath 18 does not need to be compressed to expand its diameter, but the sheath 18 does need to be capable of expanding with the balloon. Thus, if a coating is applied to the sheath 18, it should not limit the ability of the sheath 18 to expand.

Figure 9:
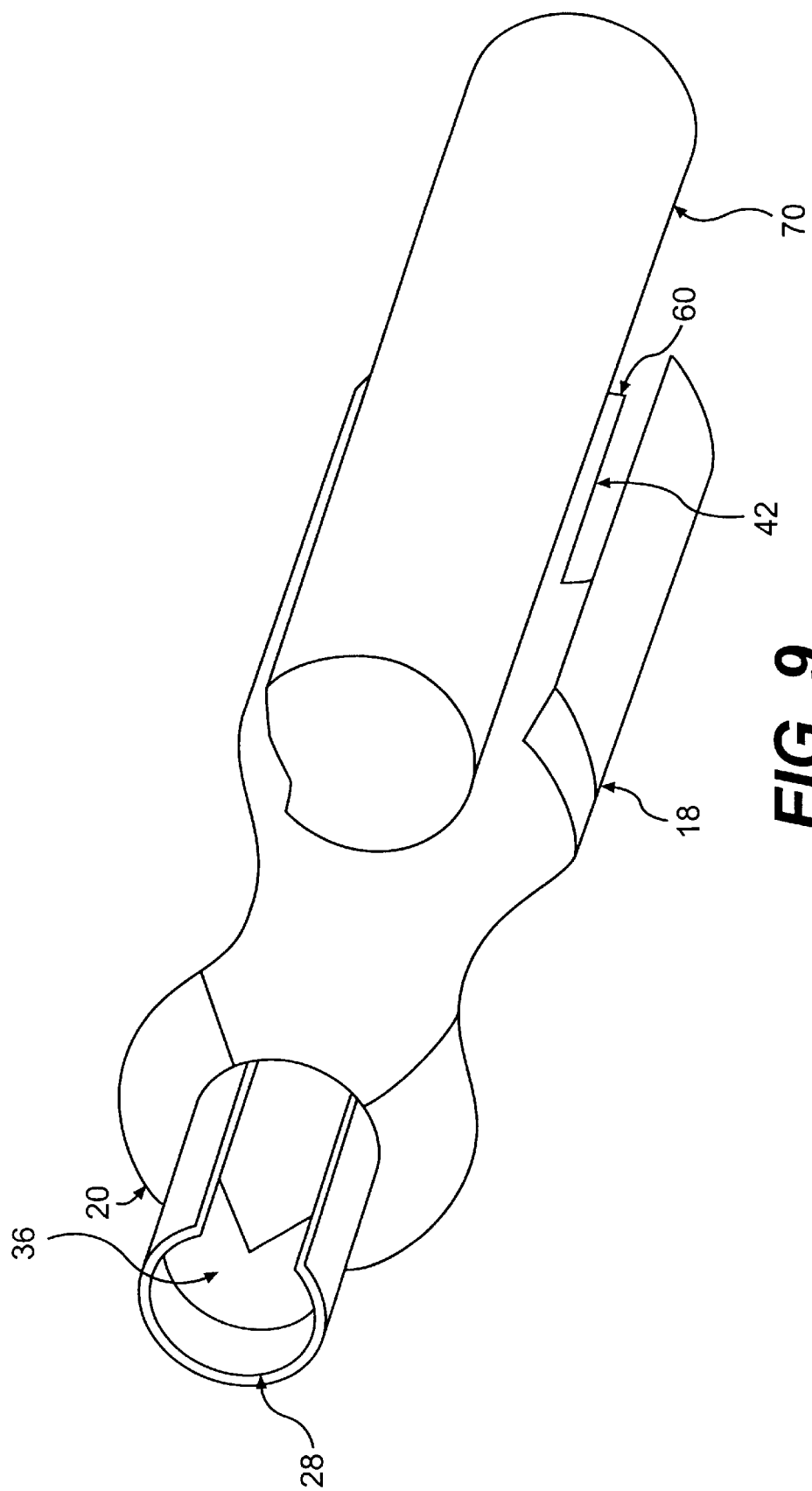
FIG. 9 is a perspective view of the present invention being used with a bougie or dilator and with a portion of the sheath cut away.

FIG. 9 illustrates an alternative embodiment which can be used in accordance with a method utilizing bougie dilation. In this method, the endoscope 16 and sheath 18 in the figure are introduced into the gastrointestinal tract. The endoscope 16 is removed. Then, the sheath 18 is re-expanded by holding the channel 42 at its proximal end 60 and pushing the sheath 18 toward its distal end 20 to expand its diameter. At the stricture, the sheath 18 only expands to the limits the stricture imposes on it. A small bougie or dilator 70 is introduced to dilate the stricture, while the sheath 18 acts as a protective shield and guide for the bougie 70 to follow. The bougie 70 is inserted past the stricture allowing the diameter of the bougie 70 to force the stricture to expand to the diameter of the shaft of the bougie 70. This procedure can be repeated with successively larger diameters of each bougie 70, until the diameter of the stricture reaches a desired value.

Figure 10:
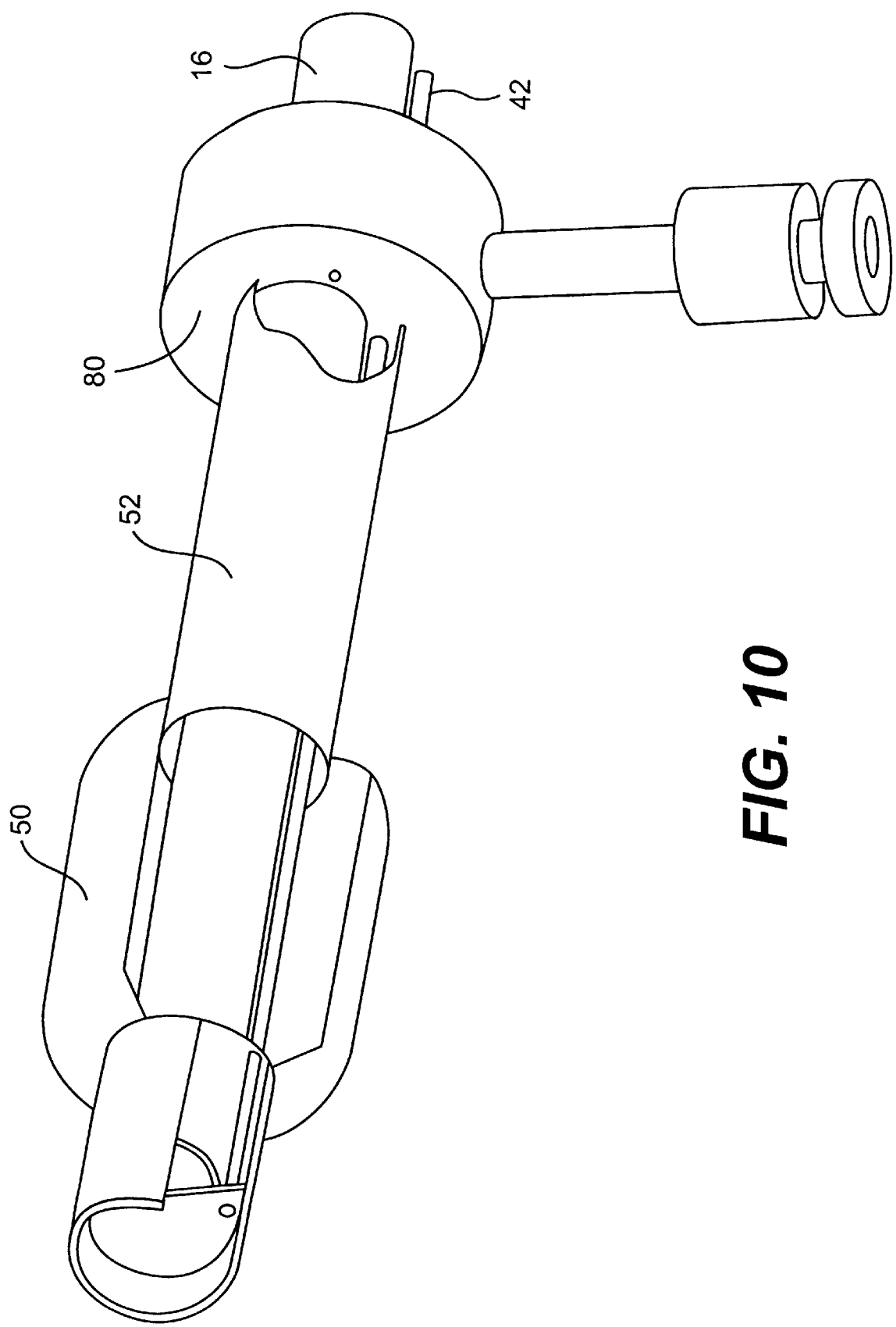
FIG. 10 is a perspective view of the present invention with a distal portion of the sheath expanded and with a device on the proximal end for inflating the distal portion of the sheath.

FIG. 10 shows another embodiment of the present invention. The device is similar to the device of FIG. 3 in that the distal portion 50 of the sheath 18 can expand, while the proximal portion 52 of the sheath 18 cannot. Instead of pushing the proximal portion 52 of the sheath 18 to expand the diameter of the distal portion 50, a proximal fitting 80 is used to seal around the endoscope 16 and channel 42 to enable the inflation of the distal portion 50 of the sheath 18 to a higher pressure for the purpose of dilation of strictures. The proximal fitting 80 includes an inflation port 82 and a medical hub 84.

Figure 11:
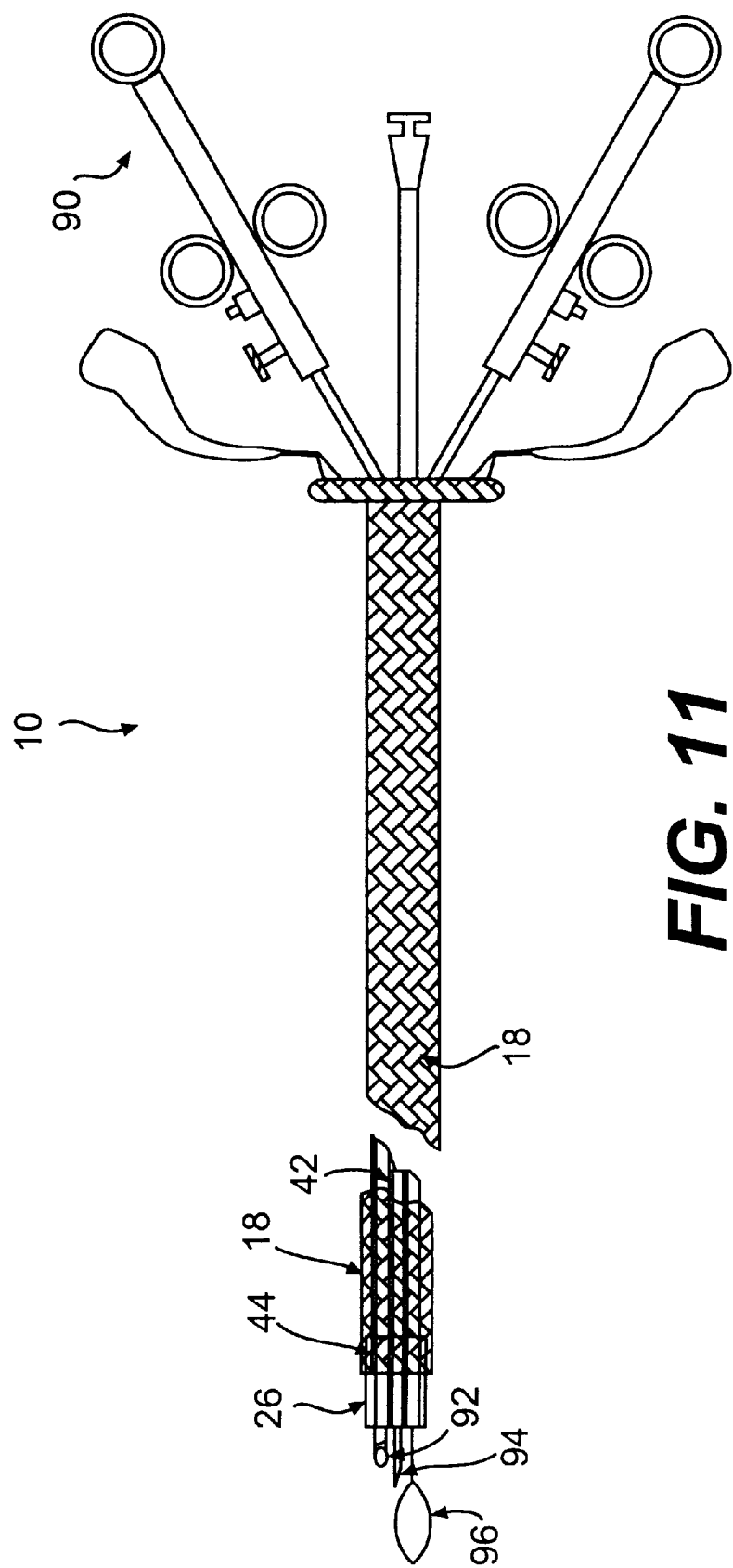
FIG. 11 is a side view of the present invention with a forceps, snare, sclerotherapy needle and suction adaptor (endoscope not shown).

Another embodiment of the present invention is depicted in FIGS. 11–13. Referring to FIG. 11, the assembly 10 includes the mesh sheath 18 shown with several instruments (collectively 90) within channels 42. In this embodiment, by way of example, the instruments 90 included are a forceps 92, a sclerotherapy needle 94, a snare 96 and a distal housing 26 having a suction chamber 28. The channels 42 and the mesh sheath 18 are attached to the distal housing 26. The sheath 18 assembly 10 can be set up for a certain procedure. For a mucosectomy, for example, the mesh sheath 18 would be equipped with a minimum of a snare 96, suction, and a sclerotherapy needle 94.

FIGS. 12 and 13 illustrate expansion of the mesh sheath 18 in diameter as it is compressed (FIG. 12) and contraction in diameter as it is in tension or allowed to return to its relaxed state (FIG. 13). The handles 98 of the instruments 90 are operated by the physician external to the patient and external to the sheath 18 to facilitate the maneuverability of the handles.

The channels 42 include additional working channels 42 for the endoscope 16. The additional channels 42 (FIG. 5) could be used for suction, infusion, or to provide access for instruments 90 such as a forceps 92, sclerotherapy needle 94, snare 96 or cautery devices (not shown) to be used in conjunction with each other rather than on an individual basis. The present invention could be provided without instruments 90 or with instruments 90.

The endoscope 16 and the channels 42 or both may be hermetically sealed within the mesh sheath 18. In one embodiment, the mesh sheath 18 itself is sealed with a urethane or similar expandable complex in such a way that it is impervious to water and air but retains its ability to expand and contract, as discussed above. In another embodiment, the mesh sheath 18 is an open mesh, but the endoscope 16 is enclosed in a baggy condom, tube or similar device (not shown) to ensure contaminants do not reach the endoscope 16. If a baggy condom or tube is used, the end should be clear so that the endoscope 16 can view the interior of the patient. The baggy condom will allow the endoscope 16 to be easily slipped into the condom, yet will conform to the outside of the endoscope 16 when the mesh sheath 18 closes around it.

Although the endoscope may be free of contaminants, the channels 42 can become, contaminated by coming into contact with body tissues and fluids during a procedure. The mesh sheath 18 provides some protection from the elements, especially if coated with an impervious material. If the channels 42 become contaminated with each use, the channels 42 can be made from a less resistant, less expensive material so that they can be disposed of after each use along with the mesh sheath 18.

Additionally, the mesh sheath 18 provides a flexible and durable outer layer that can be coated to create a gas- and liquid-impervious membrane if desired. The ability of the mesh 18 to expand laterally when compressed axially allows for easy insertion and removal of the endoscope 16 and working channels 42 within the sheath 18. It also provides an easy way to expand the diameter of the distal end 14, or any other area, of the endoscopic assembly 10. This ability to expand and retract is important for carrying out the functions mentioned above, namely dilation, anchoring and sampling. It also allows the endoscope 16 to be inserted, removed or exchanged both external and internal to the patient with diminished risk of contamination.

Another advantage of the present invention is that a lesion or disease can be treated with a single placement of the endoscope 16 instead of additional exchanges. Exchange includes removing the endoscope 16 from the patient, exchanging instruments 90, reintroducing the endoscope 16, and locating and repositioning at the desired site. An example of one procedure may include one instrument holding and stretching a lesion while the another instrument cuts it. The suction chamber 28 is also designed according to the present invention where it can hold on to lesions while other instruments 90 perform other operations. In addition, different combinations of instruments 90 can be exchanged in the channels 42 without removing the endoscope 16 from the patient. The examples are purely exemplary of the present invention.

It will be apparent to those skilled in the art that various modifications and variations can be made in the method of using the endoscopic assembly of the present invention and in construction of this assembly without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical sheath comprising:
   an elongated flexible tube adapted to coaxially enclose circumferentially a portion of a surgical device that inserts within a body cavity;
   the elongated tube having at least a distal portion that is laterally expandable within said body cavity and adapted for axial extension to lengthen or retraction to shorten the longitudinal dimension of the tube while respectively diminishing or enlarging the radial dimensions thereof; and
   at least one of a channel and a pull wire coupled to a distal end of the laterally expandable portion of the outer tube, wherein said at least one of the channel and pull wire is configured such that a force applied to at least one of the channel and pull wire in a proximal direction applies a proximally directed force to the distal end of the expandable portion, the proximally directed force applied to the distal end of the expandable portion being combined with a distally directed force applied to a proximal end of the expandable portion to cause the shortening of the longitudinal dimension of the tube and the enlarging of the radial dimensions of the expandable portion.

2. The sheath according to claim 1 wherein said laterally expandable portion of the tube has a mesh configuration.

3. The sheath according to claim 1 wherein the surgical device is an endoscope.

4. The sheath according to claim 1 wherein means are attached to a proximal end of the sheath to axially extend the sheath into tension.

5. The sheath according to claim 1 wherein the tube has a distal end with a housing disposed thereon having a distal portion that accommodates a suction chamber and a proximal portion with a surgical device entry chamber.

6. The sheath according to claim 1 wherein the sheath is hermetically sealed.

7. The sheath according to claim 1 wherein said elongated tube is substantially entirely formed of laterally expandable mesh.

8. A surgical assembly comprising:
    an elongated flexible outer tube;
    a surgical device coaxially disposed within the elongated tube;
    one or more elongated passages aligned axially within the outer tube;
    the elongated outer tube having at least a distal portion that is laterally expandable within a body cavity and adapted for axial extension to lengthen or retraction to shorten the longitudinal dimension of the tube while respectively diminishing or enlarging the radial dimensions thereof.

9. The assembly according to claim 8 wherein said laterally expandable portion of the tube comprises a mesh material.

10. The assembly according to claim 8 wherein the surgical device is an endoscope.

11. The assembly according to claim 8 wherein means are attached to a proximal end of the sheath to axially extend the sheath into tension.

12. The assembly according to claim 8 wherein the tube has a distal end with a housing disposed thereon having a distal portion that accommodates a suction chamber and a proximal portion with a surgical device entry chamber.

13. The assembly according to claim 8 wherein the surgical device is projected beyond a distal end of the tube.

14. The assembly according to claim 8 having one to five working channels.

15. The assembly according to claim 8 wherein a window is located on a distal end of the assembly.

16. The assembly according to claim 8 wherein the elongated passages include a passage for medical instruments to pass therethrough.

17. The surgical assembly of claim 8 wherein said elongated tube is substantially entirely formed of laterally expandable mesh.

18. The assembly according to claim 8, wherein the surgical device is directly positioned in an interior portion of the outer tube.

19. The assembly according to claim 8, wherein said one or more passages include at least one channel extending within the outer tube, wherein the at least one channel is configured to permit passage through the channel of at least one of fluid and an instrument while the surgical device is within the outer tube.

20. The assemby according to claim 19, wherein a distal end of the channel is coupled to a distal end of the laterally expabdable portion of the outer tube, and wherein the channel is coinfigured such that a force applied to the channel in a proximal direction applies a proximally directed force to the distal end of the expandable portion, the proximally directed force applied to the distal end of the expandable portion being combined with a distally directed force applied to a proximal end of the expandable portion to cause the shortening of the longitudinal dimension of the tube and the enlarging of the radial dimensions of the expandable portion.

21. The assembly according to claim 8, further commprising at least one of a channel and a pull wire coupled to a distal end of the laterally expandable portion of the outer tube, and wherein said at least one of the channel and pull wire is configured such that a force applied to said at least one of the channel and pull wire in a proximal direction applies a proximally directed force t the distl end of the expandable portion, the proximally directed force applied to the distal end of the expandable portion being combined with a distally directed force applied to a proximal end of the expandable portion to cause the shortening of the longitudinal dimension of the tube and the enlarging of the radial dimensions of the expandable portion.

22. A method of using surgical assembly to position a surgical device in the interior of a patient, the assembly having an enlongated flexible outer tube, at least a distal portion of the outer tube being adapted for axial extension to lengthen or retraction to shorten the longitudinal dimension of the tube while respectively diminishing or enlarging the radial dimensions thereof within said patient interior, comprising the step of:
    placing a surgical device having a distal end within the enlongated flexible tube of the assembly;
    inserting the tube, with the surgical device disposed within it, into the interior of the patient; and
    enlarging the radial dimensions of said tube, wherein the enlarging includes shortening the longitudinal dimension of the the tube to cause enlargement of the radial dimensions of the tube.

23. The method of claim 22, wherein the shortening of the longitudinal dimension includes pushing a proximal end portion pf the tube in a distal direction.

24. A method of using a surgical assembly to position a surgical device in the interior of a patient, the assembly having an elongated flexible outer tube, at least a distal portion of the outer tube being adapted for axial extension to lengthen or retraction to shorten the longitudinal dimension of the tube while respectively diminishing or enlarging the radial dimensions thereof within said patient interior, comprising the steps of:
    placing a surgical device having a distal end within the elongated flexible tube of the assembly;
    inserting the tube, with the surgical device disposed within it, into the interior of a patient;
    enlarging the radial dimensions of said tube;
    inserting one or more medical instruments through one or more elongated passages running alongside the surgical device, so that the instruments extend beyond the distal end of the assembly; and
    using the instruments to perform procedures within the patient.

25. The method according to claim 24 wherein a procedure performed within the patient includes the taking of a biopsy.

26. A method of using a surgical assembly comprising a surgical device coaxially disposed within an elongated, flexible tube, comprising the steps of:
    placing the surgical device within the elongated flexible tube having a mesh configuration;
    inserting the assembly into the interior of a patient; and
    compressing the tube longitudinally to expand the tube laterally within the patient until the tube touches the interior of the patient, whereby the tube acts to anchor the assembly, take samples from the patient's interior, or dilate a stricture in said interior.

27. The method according to claim 26, wherein the tube includes a non-expandable portion at a proximal end and an expandable section at a distal end.

28. A method of using a surgical assembly comprising a surgical device coaxially disposed within an elongated flexible tube having the ability to expand, comprising the steps of:

placing the surgical device within the elongated flexible tube having the ability to expand;

inserting the assembly into the gastrointestinal tract of a patient;

removing the surgical device from the assembly while the assembly remaining in the patient; and inserting cylindrical rods of increasing diameter in the tube until a desired diameter is achieved.

29. The method of claim 28, wherein the surgical device is an endoscope.

30. A method of using a surgical assembly comprising a surgical device coaxially disposed within a hermetically sealed, flexible tube, comprising the steps of:

placing the surgical device within the hermetically sealed flexible tube having the ability to expand;

inserting the assembly into the interior of a patient;

attaching a proximal end of the hermetically sealed tube to a source of pressurized air; and inserting pressurized air into the tube to expand its diameter.

31. The method according to claim 30, wherein the tube includes a non-expandable portion at a distal end and an expandable section at a proximal end, so that only the expandable section expands as the pressurized air is inserted into the assembly.

32. A surgical sheath comprising:

an elongated flexible tube including an interior portion adapted to coaxially enclose circumferentially a portion of a surgical device that inserts within a body cavity;

the elongated tube having at least a distal portion that is laterally expandable within said body cavity and adapted for axial extension to lengthen or retraction to shorten the longitudinal dimension of the tube while respectively diminishing or enlarging the radial dimensions thereof; and at least one channel extending within the interior portion of the tube, wherein the at least one channel is configured to permit passage through the channel of at least one of fluid and an instrument while the surgical device is within the tube, the channel being in communication with an opening at a distal end of the tube.

33. The surgical sheath according to claim 32, wherein a distal end of the interior portion is hermetically sealed.

34. A surgical sheath comprising:

an elongated flexible tube including an interior portion adapted to coaxially enclose circumferentially a portion of a surgical device that inserts within a body cavity, wherein the interior portion is hermetically sealed at a distal end of the tube;

the elongated tube having at least a distal portion that is laterally expandable within said body cavity and adapted for axial extension to lengthen or retraction to shorten the longitudinal dimension of the tube while respectively diminishing or enlarging the radical dimensions thereof.

35. The surgical sheath of claim 34, further comprising a window located at the distal end of the interior portion.

36. A surgical sheath comprising:

an elongated flexible tube adapted to coaxially enclose circumferentially a portion of a surgical device that inserts within a body cavity;

the elongated tube having at least a distal portion that is laterally expandable within said body cavity and adapted for axial extension to lengthen or retraction to shorten the longitudinal dimension of the tube while respectively diminishing or enlarging the radial dimensions thereof; and means for applying a proximally directed force to a distal end of the expandable portion, the proximally directed force applied to the distal end of the expandable portion being combined within a distally directed force applied to a proximal end of the expandable portion to cause the shortening of the longitudinal dimension of the tube and the enlarging of the radial dimensions of the expandable portion.

* * * * *

UNITED STATES PATENT AND TRADEMARK OFFICE
CERTIFICATE OF CORRECTION

PATENT NO.    : 6,293,909 B1
DATED         : September 25, 2001
INVENTOR(S)   : Michael S.H. Chu et al.

It is certified that error appears in the above-identified patent and that said Letters Patent is hereby corrected as shown below:

Column 8, claim 1,
Line 51, after "to", insert -- said --.

Column 9, claim 21,
Lines 66 and 67, replace "commprising" with -- comprising --.

Column 10, claim 21,
Line 5, replace "t the distl" with -- to the distal --.

Column 10, claim 22,
Line 12, after "using", add -- a --.
Line 19, replace "step" with -- steps --.

Column 10, claim 23,
Line 30, replace "pf" with -- of --.

Column 11, claim 28,
Line 10, replace "remaining" with -- remains --.

Column 12, claim 34,
Line 19, replace "radial" with -- radical --.

Signed and Sealed this

Twenty-sixth Day of February, 2002

*Attest:*

JAMES E. ROGAN
*Attesting Officer*  *Director of the United States Patent and Trademark Office*